United States Patent [19]
Earle

[11] Patent Number: 5,639,239
[45] Date of Patent: Jun. 17, 1997

[54] DENTAL DENTIN BONDING SYSTEM

[76] Inventor: Jeffrey O. Earle, 106 Haven Lake Ave., Milford, Del. 19963

[21] Appl. No.: 372,036

[22] Filed: Jan. 12, 1995

[51] Int. Cl.$^6$ .................................................. A61C 5/08
[52] U.S. Cl. ............................................................ 433/218
[58] Field of Search .................................. 433/218, 219, 433/226, 228.1

[56] References Cited

U.S. PATENT DOCUMENTS

| | | | |
|---|---|---|---|
| 3,509,089 | 4/1970 | Dougherty | 260/41 |
| 3,797,114 | 3/1974 | Wiland | 32/12 |
| 3,861,041 | 1/1975 | Bell | 433/219 X |
| 3,926,646 | 12/1975 | Inoue | 433/226 X |
| 4,200,980 | 5/1980 | Johnston | 433/8 |
| 4,364,731 | 12/1982 | Norling et al. | 433/218 |
| 4,514,342 | 4/1985 | Billington et al. | 260/952 |
| 4,654,007 | 3/1987 | Sigler et al. | 433/226 |
| 4,657,941 | 4/1987 | Blackwell et al. | 522/14 |
| 4,772,325 | 9/1988 | Kwan et al. | 433/219 X |
| 4,775,592 | 10/1988 | Akahane et al. | 428/406 |
| 4,813,874 | 3/1989 | Jensen | 433/219 |
| 4,814,423 | 3/1989 | Huang et al. | 528/230 |
| 4,816,495 | 3/1989 | Blackwell et al. | 522/14 |
| 4,877,402 | 10/1989 | Hirabayashi et al. | 433/218 |
| 5,141,560 | 8/1992 | Combe et al. | 433/228.1 X |
| 5,154,613 | 10/1992 | Cohen | 433/228.1 |
| 5,183,397 | 2/1993 | Weissman | 433/215 |
| 5,273,574 | 12/1993 | Arnold | 106/35 |

OTHER PUBLICATIONS

"Advances in Dental Research", vol. 6, Sep. 1992.

*Primary Examiner*—Nicholas D. Lucchesi
*Attorney, Agent, or Firm*—Myers Liniak & Berenato

[57] ABSTRACT

A method and system for attaching, for example, an artificial dental prosthetic device such as a crown, cap, or bridge to a prepared tooth structure utilizes a fluoride releasing dentin bonding system in combination with a cement layer. The dentin bonding system is first applied to the prepared tooth structure, the dentin bonding system including a primer layer and a VLC microfill composite resin layer in certain embodiments. Then the artificial prosthetic device (e.g. crown) is removably adhered to the prepared tooth structure and the dentin bonding system by way of the cement (e.g. zinc oxide based type). The cement layer sandwiched between the attached device and the dentin bonding system has a shear function less than that of the device and the dentin bonding system but sufficient to permanently bond the device to the tooth and dentin bonding system during masticatory functions and demands, thereby permitting the device to be removed or sheared from the tooth (and dentin bonding system) without destroying either. Thus, the artificial prosthetic device can be removed from the prepared tooth structure in the event that the need to do so arises (e.g. if non-functionality during mastication occurs or if endodontic responses develop).

8 Claims, 1 Drawing Sheet

DENTAL DENTIN BONDING SYSTEM

This invention relates to a dentin bonding system. More particularly, this invention relates to a method of attaching a dental device (e.g. crown, bridge, cap, filling, etc.) to a prepared tooth structure and a system for implementing same so as to protect both the prepared tooth structure from recurrent caries and the integrity of the dental device once it is attached to the tooth structure.

BACKGROUND OF THE INVENTION

Prosthetic dentistry involves the construction of crowns, caps, inlays, onlays, partial dentures, full dentures, implants, occlusion maintaining restorations, and fixed bridgework. The practice of prosthetic dentistry often requires recording accurate impressions (or molds) of a particular tooth, teeth, or implant for which an artificial prosthetic will then be fabricated at a dental laboratory. At the interface or limit line of the tooth (or root, or implant) surface to be worked on and the gingival margin (gum line), prior to impression taking, the gingival sulcus is often reflected or retracted with gingival retraction cord before flowing impression materials onto the tooth, teeth, or implant interface in order to register an accurate impression of the prepared tooth (or root, or implant) structure.

Following the taking of an impression in prosthetic dentistry, artificial prosthetic devices such as crowns, inlays, gold onlays, caps, dentures, implants, bridges, etc., are fabricated in a dental laboratory according to a master model poured from the impression. Following dental laboratory prosthetic fabrication, the prosthetic device is then delivered to the patient.

At delivery to the patient and during insertion of the prosthetic device onto or into the tooth structure, various cements are used to lute the interior portion of the artificial prosthetic (e.g. crown) to the prepared tooth which previously has been devoided of enamel and some dentin following "drilling" with, for example, water cooled dental burs attached to conventional high or low speed dental handpieces.

"Lute" and "luting" are art recognized terms which describe the attachment of dental materials or devices to one another and to prepared tooth structure by increasing the coefficient of friction between such materials or devices and tooth structure.

FIG. 1 is a side elevational cross-sectional view of a prior art tooth including crown 1 attached to prepared tooth structure 3. As shown, tooth structure 3 includes pulp 5 and extends upwardly from gingiva or gum line 7. Crown 1 is attached to prepared tooth structure 3 via cement or adhesive layer 9.

In clinical dental practice, an ongoing major concern is "washout" of cement 9 from gap 11. Gap 11 is that area which exists at the general level of the gingival cavosurface margin between prepared tooth structure 3 and the gingival limit of artificial crown 1. "Washout" is the dissolution of cement 9 via enzymatic, salivary, gingival crevicular fluid, mechanical or bacteriologic action. "Washout" leads to exposure of the soft part of the tooth structure, namely dentin 13 which may then erode and become subject to the colonization of caries (decay) producing bacteria at the junction between the interior surface of the crown and the prepared tooth structure's gingival limit. When such recurrent marginal or submarginal caries occur, the tooth is placed at increased risk of penetration of bacteria into the dentin and subsequently the dental pulp resulting in endodontic (root canal) disease, bone infection, crown or bridge loosening, breakage of the crown or bridge prosthesis, and possible tooth or bridge loss. Thus, cement "washout" and its sequela of bacterial colonization in gap 11 is a significant concern which needs to be addressed.

In response to the problem of cement "washout", various glass ionomer (GI) cements 9, which permanently adhere prosthetics to prepared tooth structures, have been developed. Many GI cements are of the visible light cured (VLC) and self-curing type which provide cross-linkage in adhering materials to one another. Several of these known glass ionomer cements are formulated to combat washout and bacterial colonization by continually releasing fluoride so as to aid in the prevention of submarginal gingival caries following the placement of crowns or bridges in patients' mouths.

A problem associated with fluoride releasing GI cements is that they must be placed onto the prepared tooth structure when it is completely dry, and moisture must then be kept from the prosthetic prepared area for about 5–10 minutes in order to allow the GI cement to properly set. This condition is difficult to achieve due at least in part to the natural moisture inside the mouth created by the salivary glands, the natural ambient mouth moisture and due to the flow of gingival crevicular fluid within the periodontal sulcus or space.

An additional problem associated with the use of known glass ionomers or other similar prosthetic luting cements is that once these cements set, there is no way to remove the crown or bridge from the tooth other than to drill it off thereby destroying the prosthetic. The need to remove such a prosthetic from the tooth may arise, of course, when decay or periodontal disease develops after fixed prosthetic attachment.

A further reported problem in using these permanent cements (e.g. GI) is that there is a reported 7%–15% incidence of adverse endodontic (root canal) response associated with their use in teeth prepared for crowns and in teeth prepared as abutments for fixed partial dentures. Such adverse responses often require root canal therapy in order to retain the crown or bridge and to return the tooth to a healthy condition. When GI cements are used, for example, the crown or bridge cannot be removed for endodontic therapy except through partial or complete destruction of the crown (or cap) itself.

For example, when as shown in FIG. 1 a GI cement 9 is employed, it is often necessary to drill through the biting or occlusal surface of crown 1 in order to provide access to pulp chamber 5 of tooth 3 and its root canal(s) in order to perform root canal therapy. Thereafter, during endodontic therapy, the pulp chamber is subsequently enlarged inside of the remaining tooth structure thereby removing a significant portion of the previously prepared internal tooth structure which supports the crown or bridge which compromises the strength of the overall tooth root and crown during normal masticatory or parafunctional tooth contact. Root canal therapy using thin sterilized stainless steel files is then performed with eventual sealing of the root canal(s) using biocompatable endodontic sealing materials and cements.

Clearly, should root canal therapy be necessary in a tooth which has been restored with, for example, a crown which has been luted to the prepared tooth structure with a GI or other similar cross-linking cement, additional removal of internal supporting tooth structure which supports the crown or bridge decreases the biological support for the crown or bridge thereby placing the crown, bridge, etc. and tooth at increased risk for breakage or loss. It therefore would be desirable and easier if the practitioner did not have to drill through crown 1 in order to access pulp 5 of tooth 3 in order to perform endodontic therapy.

In order to overcome the above described problems associated with the use of GI cements, the use of zinc oxide based luring cements 9 has sometimes been advocated. Accordingly, when zinc oxide based luting cements 9 are used as in prior art FIG. 1, practitioners are able to remove crown 1 from tooth structure 3 if endodontic therapy is required, for example. In other words, the shear function of such cements is less than that of crown 1 and dentin 13 of structure 3 but is sufficient to adequately bond crown 1 to tooth structure 3 during masticatory or parafunctional demands so that crown 1 can be selectively sheared (i.e. removed) from structure 3 without destroying either. In such cases, crown 1 (or a fixed partial denture, etc.) can easily be removed intact due to the use of such a cement 9 and endodontic therapy can easily thereafter be performed. Following completion of root canal therapy after the intact removal of crown 1, if insufficient tooth structure remains, a restorative macrofilled resin core, or in the case of a tooth used as a bridge abutment, a laboratory fabricated cast post core, can be retrofitted to the interior portion of the crown or abutment. The post core can be cemented into the endodontically treated tooth, for example, and the original crown or bridge can be inserted easily back into the patient's mouth. Endodontic therapy following removal of the entire crown when temporary cement is used, therefore, will ensure better support for the endodontially treated tooth, root and crown, rather than weaken same as occurs when, for example, GI is used to lute prosthetics to teeth.

Unfortunately, a problem associated with the use of only zinc oxide based cements or other similar non-cross-linking cements for such applications is that "washout" again becomes a concern because such cements typically are more soluble to the influx of gingival and other oral fluids as previously described and do not release fluoride as do the aforesaid GI cements in an attempt to reduce the likelihood of washout and recurrent marginal or submarginal caries.

It is apparent from the above that there exists a need in clinical prosthetic and other dental practice (e.g. restorative dentistry) for a method and a system by which recurrent perimarginal gingival caries can be abated or prevented and which also allows for the nondestructive removal of crowns, bridges, caps, fixed partial dentures, gold onlays, fillings, etc. should, for example, adverse endodontic responses arise. In other words, there is a need for a system which would eliminate the aforesaid problems and allow practitioners to both (i) place a fluoride releasing system on the prepared tooth structure so as to prevent recurrent marginal gingival caries, and (ii) have the option to remove, for example, an artificial prosthetic device (e.g. crown) intact, should the inserted prosthetic be unaesthetic to the patient, should the crown or bridge fail to function properly in a patient's mouth after insertion, should peridontal disease develop around the tooth or around the teeth to which a bridge is attached or should an adverse endodontic response occur.

It is the purpose of this invention to fulfill the above-described needs in the art, as well as other needs which will become apparent to the skilled artisan from the following detailed description of this invention.

SUMMARY OF THE INVENTION

Generally speaking, this invention fulfills the above-described needs in the art by providing a method of adhering a dental device, such as a crown, cap, bridge, onlay, inlay, filling, or the like, to a prepared tooth structure, the method comprising the steps of:

a) preparing the tooth structure;

b) adhering a permanent dentin bonding system to the prepared tooth structure; and c) removably attaching the dental device to the prepared tooth structure and the dentin bonding system by using a cement, the cement having a shear function less than that of the dentin bonding system and the dental device but sufficient to bond said dental device to the tooth structure and the dentin bonding system during masticatory functions and demands, whereby the practitioner may remove the dental device from the tooth structure at a later date if the need to do so arises.

This invention further fulfills the above-described needs in the art by providing a tooth including an artificial prosthetic device, such as a crown, cap, or bridge, removably attached to a prepared tooth structure, the tooth comprising:

the prepared tooth structure;

a fluoride releasing dentin bonding system adhered to the prepared tooth structure; and the artificial prosthetic device removably attached to the prepared tooth structure and the dentin bonding system by way of a cement so that the artificial prosthetic device may be removed from the prepared tooth structure when the need to do so arises, the cement having a shear function less than that of the dentin bonding system and the artificial prosthetic device, but sufficient to bond the prosthetic device to the dentin bonding system during masticatory functions and demands.

This invention further fulfills the above-described needs in the art by providing a method of removably attaching an artificial prosthetic device, such as a crown, cap, or bridge, to a prepared tooth structure, the method comprising the steps of:

a) preparing the tooth structure for attachment of the artificial prosthetic device;

b) applying a primer layer to the prepared tooth structure;

c) applying a visible light curable microfill composite resin to the prepared tooth structure and onto the primer layer, the primer and the visible light curable microfill composite resin representing a dentin bonding system; and d) removably attaching the artificial prosthetic device to the prepared tooth structure and the dentin bonding system by using a dental adhesive or cement so that the artificial prosthetic device may be removed from the tooth structure if the need to do so arises, the dentin bonding system being disposed between the prepared tooth structure and the dental cement.

This invention will now be described with respect to certain embodiments thereof, accompanied by certain illustrations, wherein:

IN THE DRAWINGS

DETAILED DESCRIPTION OF CERTAIN EMBODIMENTS OF THIS INVENTION

Figure 2:
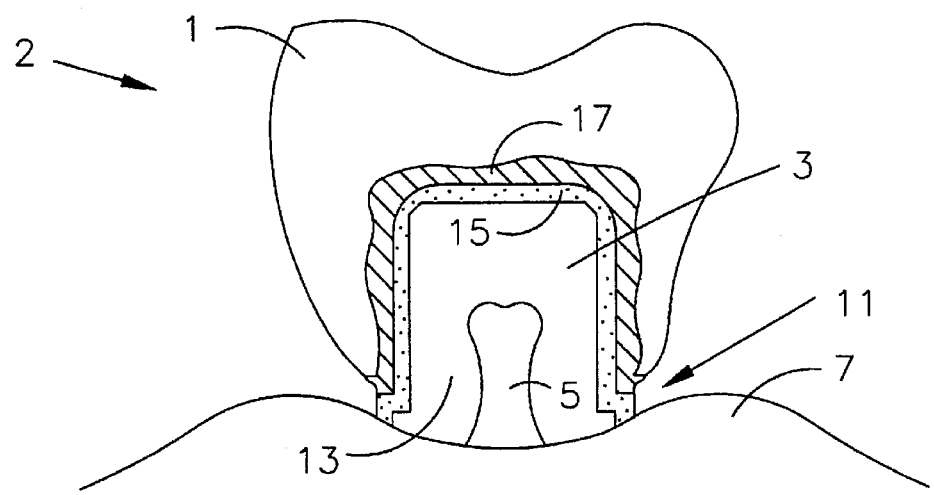
FIG. 2 is a side elevational cross-sectional view of a prepared tooth structure and a removably attached artificial crown.
Figure 3:
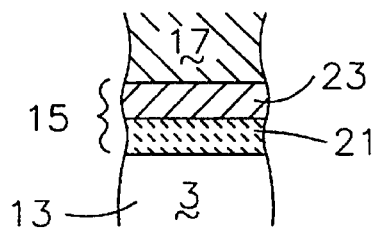
FIG. 3 is a side cross-sectional view of the adhesion system/method according to the FIG. 2 embodiment of this invention.
Figure 1:
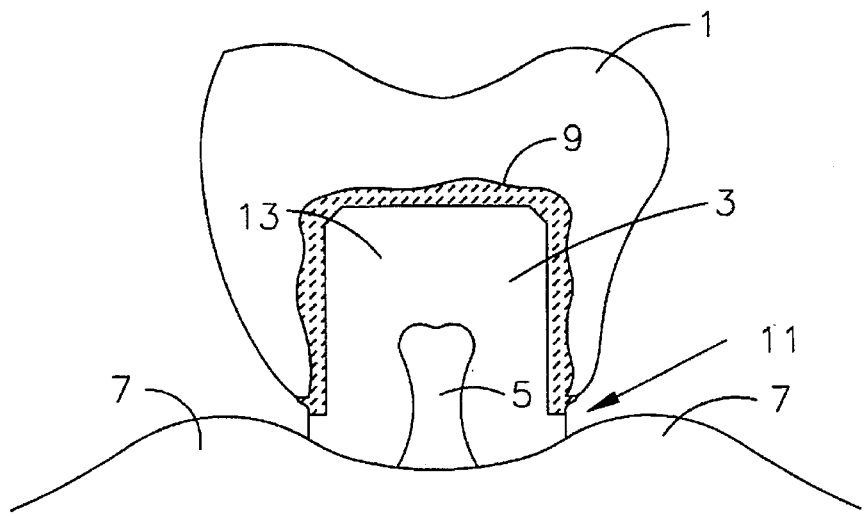
FIG. 1 is a side elevational cross-sectional view of a prior art tooth including a prepared tooth structure and an artificially attached crown.

Reference is now made to the accompanying drawings, FIGS. 2–3, in which like reference numerals indicate like parts throughout the several views.

FIG. 2 is a side elevational cross-sectional view of tooth 2 according to an embodiment of this invention. As shown, tooth 2 includes prepared tooth structure 3, pulp or pulp chamber 5, dentin 13, gingiva (gum line) 7, dentin bonding system 15, cement or adhesive layer 17, and artificial crown 1. Crown 1 is illustrated as an exemplary artificial prosthetic understood it is to be understood that any known artificial device may instead be attached to prepared tooth structure 3 instead of crown 1 in accordance with different embodiments of this invention.

Artificial crown 1 is removably attached to prepared tooth structure 3 by way of both dentin bonding system 15 and cement or adhesive layer 17. Dentin bonding system 15 is of the fluoride releasing type according to certain embodiments of this invention so as to help prevent washout and thus recurrent submarginal gingival caries near the level of gingival cavosurface margin 11. Cement layer 17 adheres crown 1 to prepared tooth structure 3 and dentin bonding system 15 so as to allow practitioners to have the ability to remove crown 1 should, for example, adverse endodontic (root canal) responses arise after attachment of the crown. The shear function of cement layer 17 is less than that of crown 1 and dentin bonding system 15 but is sufficient to permanently bond crown 1 to system 15 and tooth structure 3 during masticatory functional demands and the like so that crown 1 can be sheared (or removed) from structure 3 (and system 15) without destroying either when the need to do so later arises.

Cement 17 may be any conventional cement or other luting agent known in the art which has a shear function less than that of dentin bonding system 15 and the dental device (e.g. crown 1) attached to the tooth. For example, cement layer 17 may be of the self-curing zinc oxide based type according to certain embodiments, and/or may be ZOE 2200 commercially available from L.D. Caulk, Milford, Del., according to certain preferred embodiments. Alternatively, TempBond commercially available from Kerr may be used as adhesive 17 in certain other embodiments of this invention. Cement 17 is of the non-cross-linking type according to certain embodiments.

Dentin bonding system 15 seals prepared tooth structure 3 and is made up of two layers as illustrated in FIG. 3. Dentin bonding system 15 includes primer layer 21 and visible light cured microfill composite resin layer 23 according to certain embodiments. Primer layer 21 (e.g. acetone based) of dentin bonding system 15 may be, for example, "ProBond Primer" commercially available from L.D. Caulk, Milford, Del., according to certain embodiments of this invention. Microfill composite resin layer 23 may be of the visible light cured (VLC) type and may be, for example, "ProBond Adhesive" available from L.D. Caulk, Milford, Del. according to certain embodiments. "ProBond" primer and adhesive from L.D. Caulk are related to U.S. Pat. Nos. 4,514,342; 4,657,941; 4,814,423; and 4,816,495, the disclosures of which are hereby incorporated herein by reference.

Alternatively, fluoride releasing FLUOROCORE/FLUROSHIELD (FC/FS) or simply Fluroshield (both available from L.D. Caulk, Milford, Del.) may be used instead of or in addition to (i.e. on top of) system 15 according to certain embodiments. These materials, of course, are to be located between cement layer 17 and prepared tooth structure 3.

An advantage associated with dentin bonding system 15 is that dentin bonding primers (e.g. layer 21) often work best in moist environments. Thus, it is unnecessary to conduct strict moisture control for an extended period of time as is the case with GI cements, for example.

Composite resin layer 23 is of the VLC microfill type according to certain preferred embodiments. "Microfill" means resin layer 23 has a particle size of from about 0.01–0.1 µm. Resin layer 23 may instead be of the nanofill (0.005–0.01 µm), minifill (0.1–1 µm), or midifill (1–10 µm) type according to certain other embodiments of this invention.

Dentin 13 of prepared tooth structure 3 is a fiber reinforced tissue including minerals, collagen, and water. The mineral component is known to be mostly calcium phosphate in the form of hydroxyapatite. The preparing of tooth structure 3 exposes a substantial portion of dentin 13. The cutting of dentin 13 with a conventional rotary bur produces a smear layer of dentinal debris. Primer or etching layer 21 of dentin bonding system 15 removes the smear layer, dissolves the minerals at the surface thus exposing the collagen fiber matrix, and slightly opens the dentinal tubules as it is applied to prepared tooth structure 3 in certain embodiments. Thus, priming or etching layer 21 is applied to prepared tooth structure 3 so as to condition it for the application of composite resin layer 23.

When resin layer 23 (e.g. VLC microfill) is applied to prepared tooth structure 3 over top of primer layer 21, dentin bonding system 15 is completed. Dentin bonding system 15 is substantially thin in nature and penetrates into the dentinal tubules of dentin 13 of prepared tooth structure 3 so as to thoroughly bond itself to the prepared tooth structure. Dentin bonding system 15 is biologically and biomechanically interlocked onto the tubules of dentin 13 along the surface of prepared tooth structure 3.

Any conventional fluoride releasing agent or material may be added to dentin bonding system 15 or resin layer 23 so as to result in it becoming a fluoride releasing system or layer for the purpose of combatting washout and eliminating recurrent marginal caries. Alternatively, Fluroshield may be used instead of or in addition to (e.g. on top of) system 15 as discussed above.

When dentin bonding system 15 or resin layer 23 is of the visible light curable (VLC) type according to certain embodiments, visible light is used to cure dentin bonding system 15 after it is applied to prepared tooth structure 3. Following the curing of dentin bonding system 15, the practitioner takes the necessary impression(s) so that, for example, an artificial prosthetic device (e.g. cap, crown, denture, bridge, etc.) may be formed in a dental laboratory.

After, for example, crown 1 is formed by using the aforesaid impression taken by the practitioner following the preparing of the tooth, crown 1 is attached to tooth structure 3 and dentin bonding system 15 by way of cement layer 17. The use of cement 17, having a shear function or strength less than that of crown 1 and system 15 (and tooth 3), to attach crown 1 to tooth structure 3 results in the practitioner having the ability to nondestructively remove crown 1 at a later date if the need to do so arises.

For example, in a case where an adverse endodontic response arises long after crown 1 has been attached to tooth structure 3 according to the first embodiment, the practitioner may non-destructively remove the entire crown 1 from tooth structure 3 and system 15, and perform endodontic therapy without having to drill all the way through crown 1. The ability to remove the crown intact is due to the use of adhesive or cement layer 17 are described above. Accordingly, after the removal of crown 1 in the event that, for example, an adverse endodontic response arises, tooth structure 3 is exposed to the practitioner so as to enable easy access to pulp 5 and the tooth's root canal(s) (not shown).

Cement 17 may be of the hard zinc oxide based type according to certain embodiments of this invention. Furthermore, cement layer 17 is preferably less than about 150 µm thick according to certain embodiments. More preferably, cement layer 17 is from about 40–90 µm thick according to certain further preferred embodiments.

Dentin bonding system 15 including layers 21 and 23 is less than about 100 µm thick according to certain embodiments of this invention. More preferably, dentin bonding system 15 is from about 5–50 µm thick, and most preferably is from about 5–20 µm thick according to certain other embodiments. Thus, the overall thickness of dentin bonding system 15 and cement layer 17 combined may be from about 45–250 µm according to certain embodiments of this invention.

A typical preparation and attachment of an artificial prosthetic device (e.g. crown, cap, denture, bridge, etc.) according to the FIG. 2 embodiment of this invention will be described as follows. The practitioner (e.g. dentist) first prepares the tooth for attachment of the artificial prosthetic device (e.g. crown 1) by drilling the tooth with, for example, water cooled dental bur(s) attached to high and/or low speed dental handpieces which are conventional in the art. Much, if not all, of the enamel of the tooth is removed and dentin 13 is exposed so as to allow a substantially large bulk of prepared tooth structure 3 extending above the gingival margin as shown in FIG. 2.

Next, the practitioner applies primer layer 21 to the exposed surface of prepared tooth structure 3. Then, VLC composite resin layer 23 (e.g. of the microfill type) is applied over top of primer layer 21 onto prepared structure 3. Layers 21 and 23 make up dentin bonding system 15 which may be of the fluoride releasing type according to certain embodiments. Thereafter, dentin bonding system 15 is visible light cured in a conventional manner.

Following the visible light curing of dentin bonding system 15, the practitioner takes the necessary impression(s) of the tooth or teeth. After the artificial prosthetic device is made at a remote location, it is adhered to prepared tooth structure 3 and dentin bonding system 15 by way of cement layer 17 which may be of the self-curing zinc oxide based type according to certain embodiments.

Thus, crown 1 (or any other dental device) is removably attached/adhered to prepared tooth structure 3. Due to the use of adhering layer 17 as described above, the practitioner can non-destructively remove crown 1 intact from tooth structure 3 long after the original attachment of the crown if the need to do so arises. For example, if a patient develops adverse endodontic responses long after crown 1 has been attached to tooth structure 3, the practitioner can remove the entire crown 1 and gain easy access to tooth structure 3 and pulp 5 for the necessary therapy or surgery. Afterwards, the same crown 1 (or alternatively another crown 1) can be re-attached to prepared tooth structure 3 in accordance with certain embodiments of this invention.

While the aforesaid embodiments utilize dentin bonding system 15 and cement layer 17 in order to attach a prosthetic device to prepared tooth structure 3, the combination of dentin bonding system 15 and cement layer 17 can also be used in restorative dentistry to, for example, attach fillings or the like (e.g. amalgams, gold inlays, onlays, or VLC resins) to prepared teeth.

Once given the above disclosure, therefore, various other modifications, features, or improvements will become apparent to the skilled artisan. Such other features, modifications, and improvements are thus considered a part of this invention, the scope of which is to be determined by the following claims.

I claim:

1. A method of removably attaching an artificial prosthetic device such as a crown, cap, or bridge to a prepared tooth structure, the method comprising the steps of:
   a) preparing said tooth structure for attachment of said artificial prosthetic device;
   b) applying a primer layer to said prepared tooth structure;
   c) applying a visible light curable microfill composite resin to said prepared tooth structure and onto said primer layer, said primer layer and said visible light curable microfill composite resin forming a dentin bonding system; and
   d) removably attaching said artificial prosthetic device to said prepared tooth structure and said dentin bonding system by using a dental adhesive or cement so that said artificial prosthetic device may be removed from said tooth structure if the need to do so arises, said dentin bonding system being disposed between said prepared tooth structure and said dental cement.

2. The method according to claim 1, further comprising the step of visible light curing said dentin bonding system before carrying out said recited step d), and wherein said cement recited in step d) has a shear function less than that of said dentin bonding system and said prosthetic device but sufficient to bond said device to said dentin bonding system and said tooth structure during masticatory functions and demands.

3. The method according to claim 2, further comprising the steps of:
   applying a fluoride releasing dentin bonding system as said dentin bonding system recited in said step c); and
   applying a zinc oxide based temporary cement as said cement recited in said step d).

4. A dental bonding system including an artificial prosthetic device such as a crown, cap, or bridge removably attached to a prepared tooth structure, said system comprising:
   the prepared tooth structure;
   a fluoride releasing dentin bonding system adhered to said prepared tooth structure; and
   the artificial prosthetic device removably attached to said prepared tooth structure and said dentin bonding system by way of a cement so that said artificial prosthetic device may be removed from said prepared tooth structure when the need to do so arises, said cement having a shear function less than that of said dentin bonding system and said artificial prosthetic device, but sufficient to bond said device to said dentin bonding system during masticatory functions and demands.

5. The tooth of claim 4, wherein said fluoride releasing dentin bonding system includes a base primer layer and a visible light cured microfilled composite resin layer.

6. The tooth of claim 5, wherein said cement is self-cured and zinc oxide based.

7. The tooth of claim 5, wherein said dentin bonding system has a thickness of less than about 100 µm, and said cement has a thickness of less than about 150 µm.

8. The tooth of claim 7, wherein said dentin bonding system has a thickness of from about 5–20 µm.

* * * * *